United States Patent
Dubberstein (10) Patent No.: US 6,267,725 B1
(45) Date of Patent: Jul. 31, 2001

(54) INDIVIDUAL CHANNEL ANALOG WALL FILTERING TO IMPROVE FLOW SENSITIVITY IN ULTRASOUND IMAGING

(75) Inventor: David T. Dubberstein, Hales Corners, WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/395,343

(22) Filed: Sep. 13, 1999

(51) Int. Cl.[7] ........................................ A61B 8/00
(52) U.S. Cl. ............................ 600/443; 600/447
(58) Field of Search .................. 600/437, 441–447, 600/454–458; 128/916; 367/7, 11, 130; 73/625, 626

(56) References Cited

U.S. PATENT DOCUMENTS

| | | | |
|---|---|---|---|
| 5,349,525 | * 9/1994 | Dunki-Jacobs et al. | 600/437 |
| 5,454,372 | * 10/1995 | Banjanin et al. | 600/454 |
| 5,517,995 | * 5/1996 | Klepper et al. | 600/437 |

OTHER PUBLICATIONS

W. Walker, A New Class of Aperture Domain Flow Estimation Algorithms, 1997 IEEE Ultrasonics Symposium, pp. 1227–1231.

* cited by examiner

Primary Examiner—Francis J. Jaworski
Assistant Examiner—Ali M. Imam
(74) Attorney, Agent, or Firm—Christian G. Cabou; Phyllis Y. Price; Dennis M. Flaherty (57) ABSTRACT

A method and an apparatus for wall filtering the receive signal in each receive channel of an ultrasound imaging system prior to analog-to-digital conversion. Large-amplitude echoes corresponding to stationary or very slow-moving tissue are removed before they saturate the inputs to the analog-to-digital converters (ADCs) in the receive channels. By first removing the wall signal, the gain of the TIC amplifier in the receive channel can be increased without saturating the (ADC). This additional amplification will increase the small flow signals, mapping them into higher bits of the ADC, thereby allowing more sensitive detection of weak blood flow in the human body.

23 Claims, 4 Drawing Sheets

INDIVIDUAL CHANNEL ANALOG WALL FILTERING TO IMPROVE FLOW SENSITIVITY IN ULTRASOUND IMAGING

FIELD OF THE INVENTION

This invention generally relates to ultrasound imaging of fluid flow fields. In particular, the invention relates to a method and an apparatus for imaging blood flowing in the human body by detecting ultrasonic echoes reflected from the flowing blood.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

In standard color flow processing, a high pass filter known as a wall filter is applied to the data before a color flow estimate is made. The purpose of this filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

In the color flow mode of a conventional ultra-sound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The echo or return signals are detected by the elements of the transducer array and then formed into a receive beam by a beamformer.

For example, the traditional color firing sequence is a series of firings (e.g., tone bursts) along the same position, which firings produce the respective receive signals:

$$F_1 F_2 F_3 F_4 \ldots F_M$$

where $F_1$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point will be filtered to produce the respective difference signals:

$$(F_1 - F_2)\ (F_2 - F_3)\ (F_3 - F_4) \ldots (F_{M-1} - F_M)$$

and these differences are input to a color flow velocity estimator.

One of the primary advantages of Doppler ultrasound is that it can provide noninvasive and quantitative measurements of blood flow in vessels. Given the angle θ between the insonifying beam and the flow axis, the magnitude of the velocity vector can be determined by the standard Doppler equation:

$$v = c f_d / (2 f_0 \cos \theta)$$

where c is the speed of sound in blood, $f_0$ is the transmit frequency and $f_d$ is the motion-induced Doppler frequency shift in the backscattered ultrasound signal. The Doppler effect results in a time variation in the phase of the backscattered signal.

U.S. patent application Ser. No. 09/065,212, filed on Apr. 23, 1998, discloses a method and an apparatus for imaging flow directly in B mode. A sequence of broadband pulses is transmitted to a transmit focal position, and the backscattered signals from this sequence are filtered to remove echoes from stationary or slow-moving reflectors along the transmit path. The resulting flow signals and a conventional B-mode vector are envelope detected and displayed, the flow image being superimposed on the tissue image. A B-mode flow image is formed by repeating the above procedure for multiple transmit focal positions across the region of interest. The filtering is performed in slow time (along transmit firings) and consists of a high-pass "wall" filter (e.g., an FIR filter) with B-mode image feed-through. The firing-to-firing filtering permits a longer FIR wall filter for better clutter suppression while increasing the cutoff frequency to a useful range. The wall filter increases the flow signal-to-clutter ratio. The resulting B-mode flow image has the advantages of low clutter from stationary or slow-moving tissue or vessel walls, high resolution, high frame rate and flow sensitivity in all directions. Flow sensitivity in the range direction is highest and arises from pulse-to-pulse radiofrequency (RF) decorrelation, while flow sensitivity in the cross-range direction is due to pulse-to-pulse amplitude decorrelation as a group of reflectors (e.g. blood or contrast agents) flows across the beam profile.

Wall filtering in flow estimation is intended to remove the large-amplitude echoes produced by stationary or very slow-moving tissue. Since these large-amplitude signals are conventionally not removed until after conversion of the analog echoes into digital acoustic data, very large-amplitude echoes can saturate the input to the analog-to-digital converters incorporated in the receive channels. Thus there is a need for a technique which enables the large-amplitude echoes corresponding to stationary or very slow-moving tissue to be removed prior to analog-to-digital conversion in the receiver.

SUMMARY OF THE INVENTION

The present invention is a method and an apparatus for wall filtering the receive signal in each receive channel prior to analog-to-digital conversion. The benefit of wall filtering in every receive channel is that the large-amplitude echoes corresponding to stationary or very slow-moving tissue are removed before they saturate the inputs to the analog-to-digital converters in the receive channels.

In the typical receive channel, each line of RF echo data derived from a single transmit is first passed through a time-gain control (TGC) amplifier and then the resulting amplified analog signal is converted into a digital signal by an analog-to-digital converter. Currently, the limited dynamic range of the analog-to-digital converter makes it difficult to get both the wall signal (i.e., the large-amplitude echoes corresponding to stationary or very slow-moving tissue) and the flow signal through the analog-to-digital converter. By first removing the wall signal, the gain of the TGC amplifier can then be further increased without saturating the analog-to-digital converter. This additional amplification will increase the small flow signals, mapping them into higher bits of the analog-to-digital converter. This will increase the sensitivity of the ultrasound scanner to low-power flow, allowing more sensitive detection of weak blood flow in the human body.

In accordance with the preferred embodiments of the invention, wall filtering occurs in each receive channel of the receiver. A first RF echo signal is acquired and stored following a first transmit firing, which is steered and focused at a transmit focal position. A second RF echo signal is then acquired following a second transmit firing, which is steered and focused at the same transmit focal position. The stored first RF signal is then subtracted from the acquired second RF signal. In accordance with the preferred embodiments, this analog subtraction occurs between the pre-amplifier and the TGC amplifier.

The idea of wall filtering within each receive channel is applicable to any ultrasound imaging system. In particular, wall filtering within the receive channels can be employed in systems which perform flow estimation, whether in the B mode or the Doppler velocity or power modes (i.e., the so-called "color flow" modes).

DETAILED DESCRIPTION OF THE PREFERRED EMBODIMENTS

Figure 1:
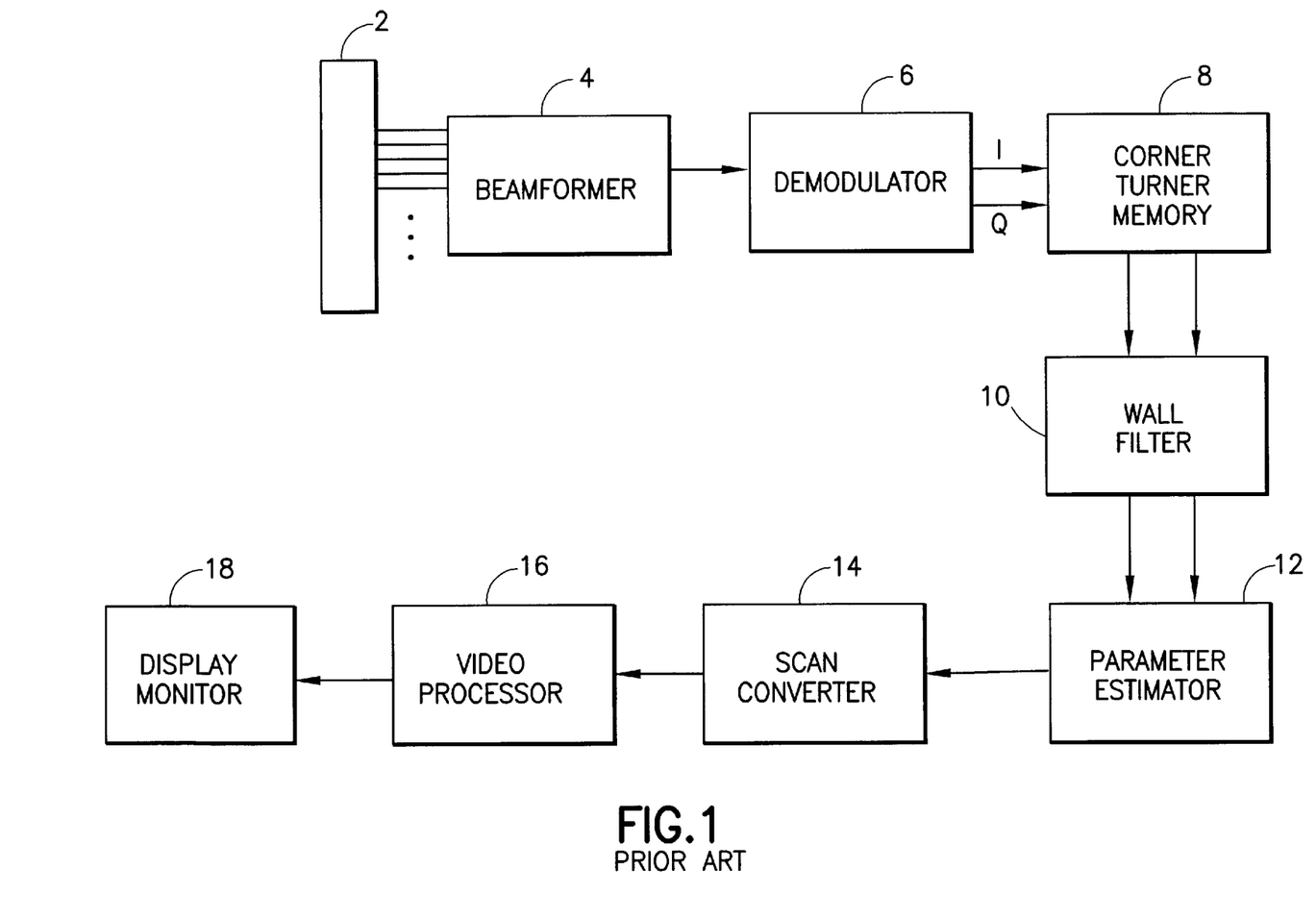
FIG. 1 is a block diagram showing the signal processing chain for a conventional color flow ultrasound imaging system.

Referring to FIG. 1, the basic signal processing chain for a color flow imaging system comprises an ultrasound transducer array 2, which is activated to transmit pulse sequences comprising tone bursts of length P which are fired repeatedly at the PRF. The RF echo signals are detected by the transducer elements and received by the respective receive channels in the beamformer 4. The beamformer sums the delayed channel data and outputs a beamsummed signal, which is demodulated into in-phase and quadrature (I/Q) signal components by a demodulator 6. The I/Q signal components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which calculates the mean flow velocity using the Doppler shift of the echo signals. In addition, parameter estimator 12 calculates the power and/or variance (turbulence) of the echo signals.

The color flow estimates are sent to a scan converter 14, which converts the color flow image data into X-Y format for video display. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

Figure 2:
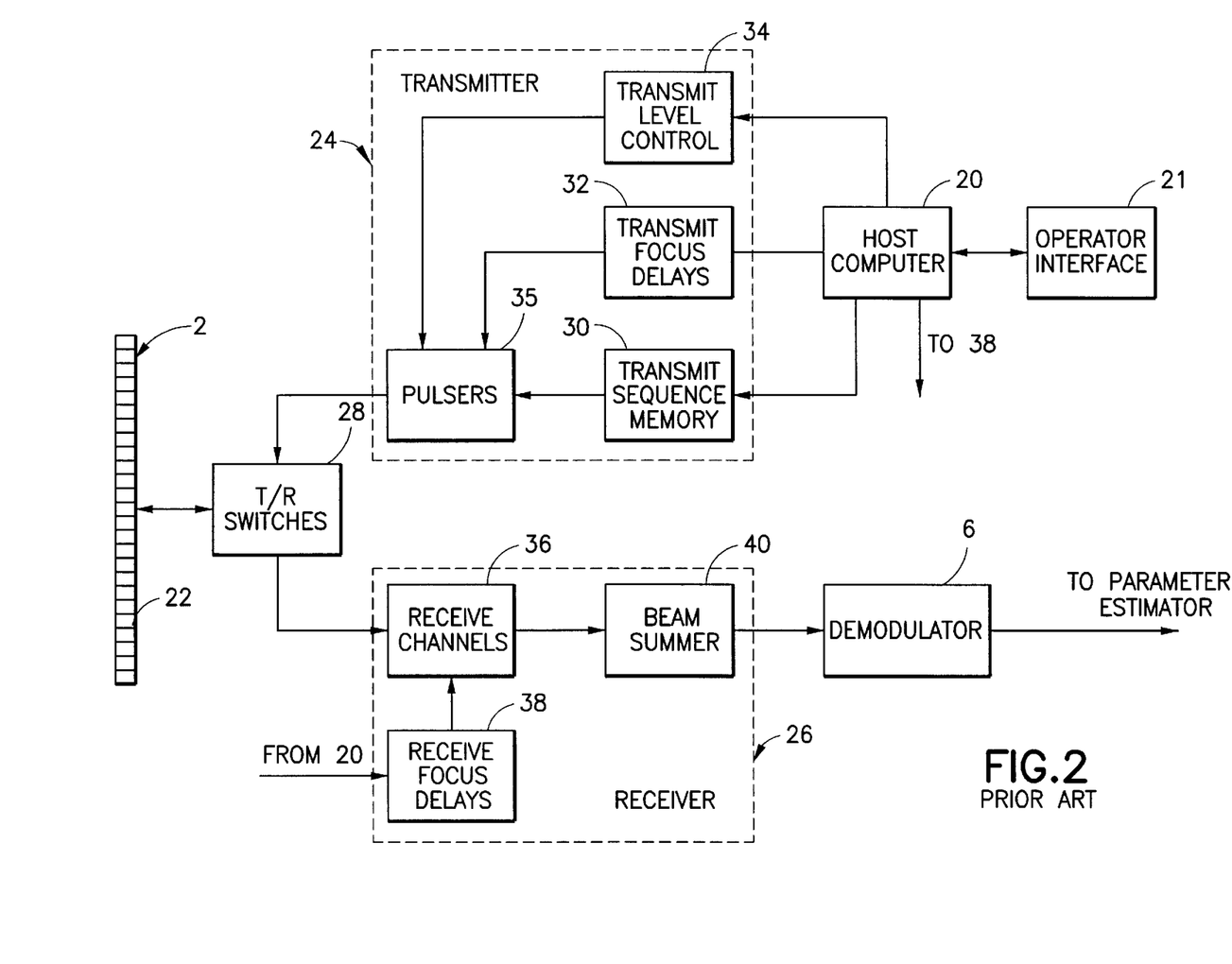
FIG. 2 is a block diagram showing the front end of a conventional color flow ultrasound imaging system.

The present invention may be incorporated in a system of the type depicted in FIG. 1 or other compatible color flow imaging systems. Referring to FIG. 2, system control is centered in a host computer (or master controller) 20, which accepts operator inputs through an operator interface 21 and in turn controls the various subsystems. The host computer 20 also generates the system timing and control signals which are distributed via various control buses. The transducer array 2 consists of a plurality of separately driven transducer elements 22, each of which produces a burst of ultrasonic energy when energized by a pulsed waveform produced by a transmitter 24. The ultrasonic energy reflected back to transducer array 2 from the object under study is converted to an electrical signal by each receiving transducer element 22 and applied separately to a receiver 26 through a set of transmit/receive (T/R) switches 28. Transmitter 24 and receiver 26 are operated under control of host computer 20. A complete scan is performed by acquiring a series of echoes in which transmitter 24 is gated ON momentarily to energize each transducer element 22, and the subsequent echo signals produced by each transducer element 22 are applied to receiver 26. A channel may begin reception while another channel is still transmitting. The receiver 26 combines the separate echo signals from each transducer element to produce a single echo signal which is used to produce a line in an image on the display monitor.

In the conventional ultrasound system, shown in FIGS. 1 and 2, adjustment of the length of the transmit pulses in each channel is implemented by programming a digital transmit sequence memory 30. Each transducer element 22 in the transmit aperture is pulsed by a pulse waveform output by a respective pulser 35 in response to a respective transmit sequence output to that pulser from the transmit sequence memory 30. The length of each pulse waveform (i.e., burst) is proportional to the number of bits in the respective digital transmit sequence. In the case of bipolar pulsers, the +1 and −1 elements of each transmit sequence are transformed into pulses of opposite phase.

Under the direction of host computer 20, the transmitter 24 drives transducer array 2 such that the ultrasonic energy is transmitted as a directed focused beam. To accomplish focusing, respective time delays are imparted to the pulsers 35 by a transmit focus delay block 32, while respective peak pulse amplitudes are set by transmit level control block 34. The host computer 20 determines the conditions under which the acoustic pulses will be transmitted. With this information, the transmit focus delay and transmit level control blocks will respectively determine the timing and the amplitude of each of the transmit pulses to be generated by the pulsers 35. The pulsers 35 in turn send the transmit pulses to respective elements 22 of the transducer array 2 via the T/R switches 28, which protect the TGC amplifiers (not shown) from the high voltages which may exist at the transducer array. By appropriately adjusting the transmit focus time delays in a conventional manner, an ultrasonic beam can be directed and focused at a transmit focal position.

The echo signals produced by each burst of ultrasonic energy reflect from objects located at successive ranges along each ultrasonic beam. Due to the differences in the propagation paths between a reflecting point and each transducer element, the echo signals will not be detected simultaneously and their amplitudes will not be equal. Receiver 26 amplifies the separate echo signals via a respective TGC amplifier (not shown in FIG. 2) in each receive channel 36. The receive channels 36 impart the proper time delays to the respective amplified echo signals. The receive time delays, like the transmit time delays, are provided under the control of the host computer. The receive time delays may be read out from look-up tables stored in random access memory 38. The receive beamsummer 40 sums the time-delayed signals to provide an echo signal which accurately indicates the total ultrasonic energy reflected from a point located at a particular range along the ultrasonic beam.

The beamsummed receive signals are output to the demodulator 6, which forms the I and Q baseband components. These baseband components are bandpass-filtered in respective receive filters (not shown), which preferably take the form of finite impulse response filters. The filter coefficients are provided to the receive filters from a filter coefficient memory (not shown) under the control of host computer 20. The bandwidth of the receive filters can be adjusted by changing the filter coefficients. The filtered outputs are then processed by the color flow processor, i.e., corner turner memory 8, wall filters 10 and a parameter estimator 12 shown in FIG. 1. As described above, the parameter estimator conventionally includes a velocity estimator which estimates velocity as a function of the phase shift in the wall-filtered backscattered signals.

Figure 3:
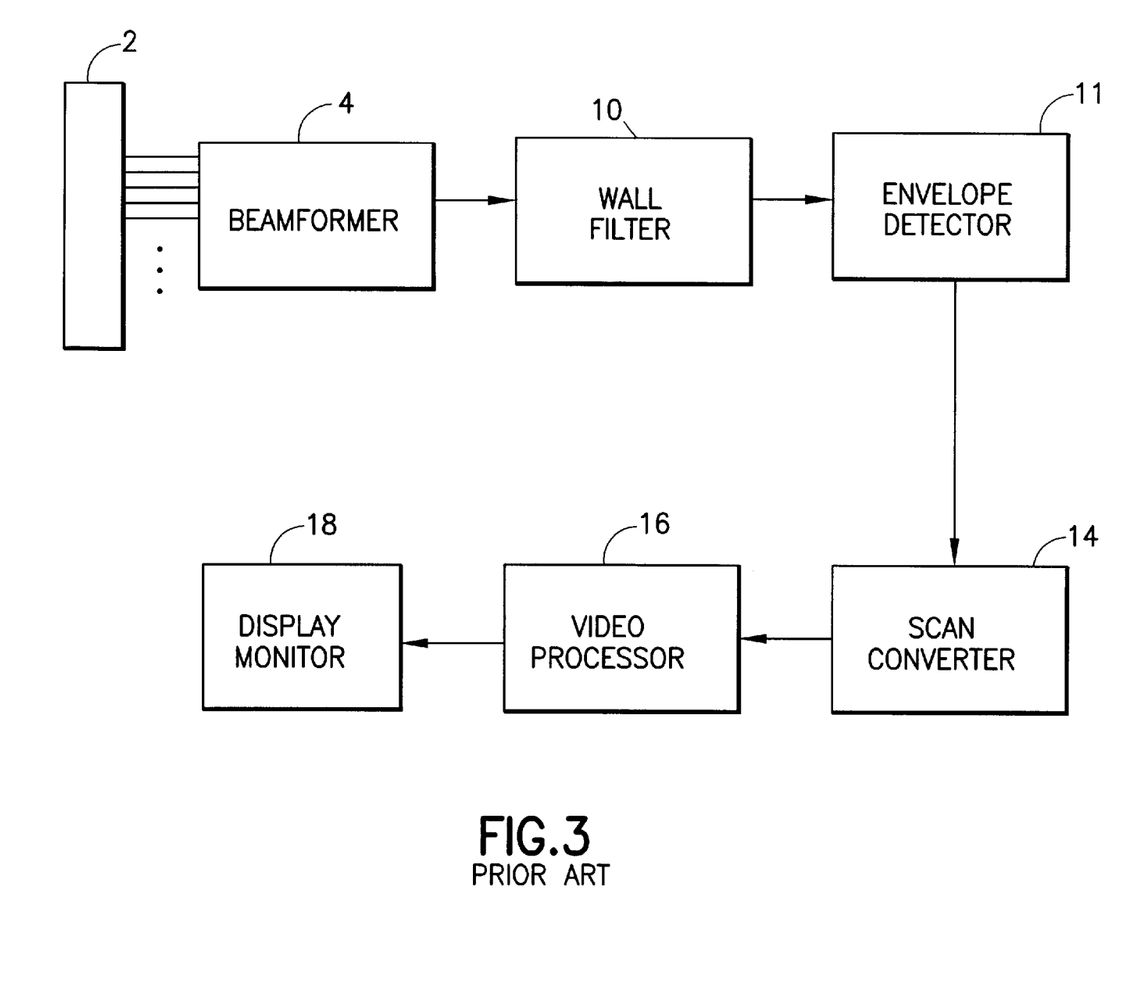
FIG. 3 is a block diagram showing the signal processing chain for a B-mode flow ultrasound imaging system.

FIG. 3 generally depicts a system for B-mode flow imaging. In this case, the summed receive signals for each of N transmit firings are output in succession to a wall filter 10, which filters across the N transmit firings and then outputs a filtered signal to detector 11. The detector 11 forms the envelope of the firing-to-firing filtered signal. After post-processing (including edge enhancement and logarithmic compression) and scan conversion, the scan-converted frames are passed to a video processor 16, which maps the video data to a display grayscale. The grayscale image frames are then sent to the video monitor 18 for display. This procedure is repeated so that a respective scan line is displayed for each transmit focal position (in the case of one transmit focal position for each beam angle) or for each transmit beam angle (in the case of multiple transmit focal positions for each beam angle).

Figure 4:
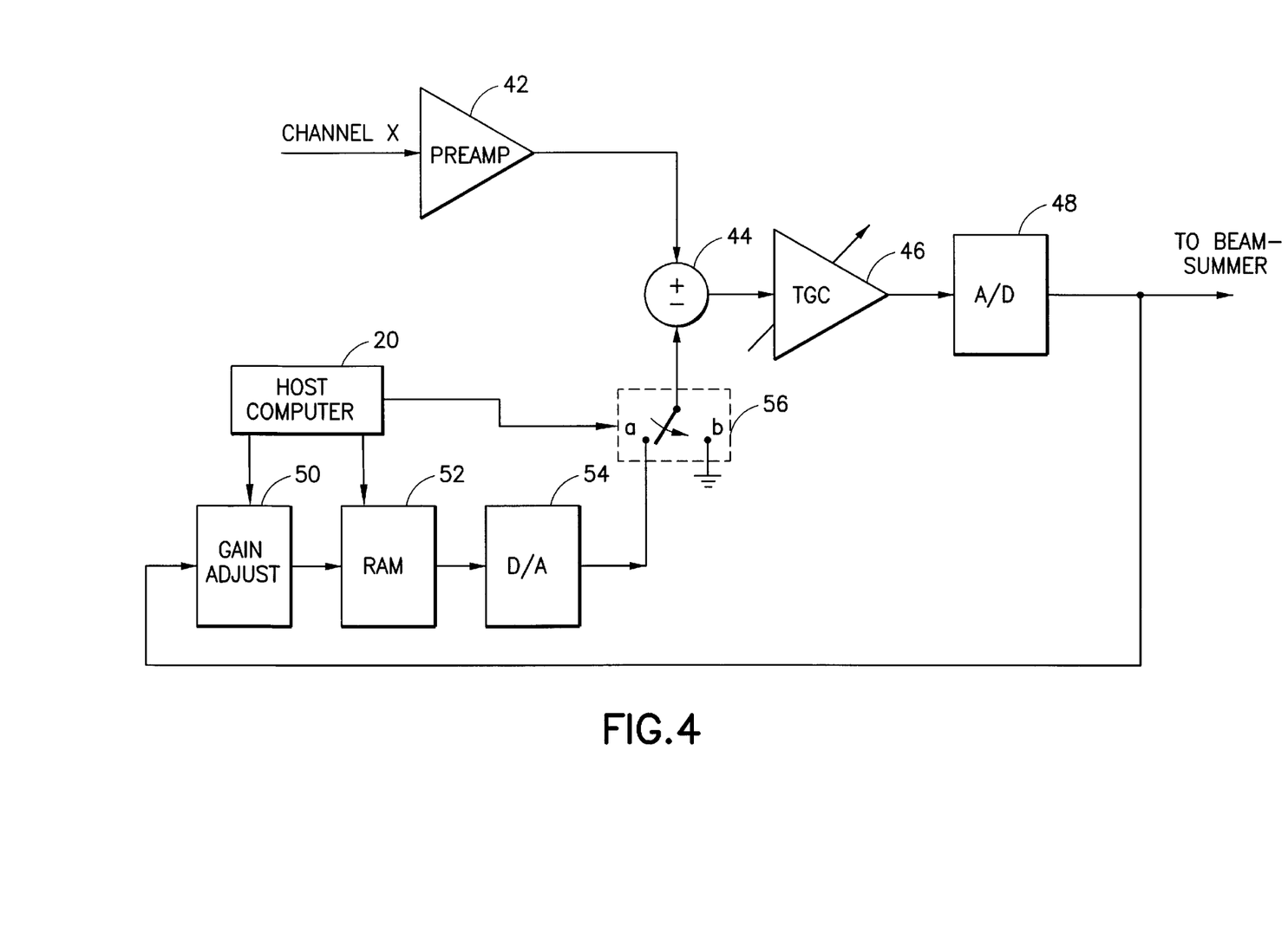
FIG. 4 is a block diagram depicting a receive channel in accordance with the preferred embodiment of the invention.

The invention can be incorporated in any ultrasound system having a receive beamformer, including the systems generally depicted in FIGS. 1 and 3. In accordance with the preferred embodiments of the invention, wall filtering is carried out in the receive channels prior to analog-to-digital conversion. A preferred implementation of the invention is shown in FIG. 4, which shows an individual receive channel.

The following discussion assumes that the transmitter is programmed by the host computer to cause the transducer array to transmit a succession of ultrasound pulses focused at a particular transmit focal position, each transmission being referred to as a "transmit firing". A succession of pulses focused at the same transmit focal position is referred to as a "packet". The receiver in turn is programmed to form a respective RF receive signal from the ultrasound echoes detected by the transducer array subsequent to each transmit firing.

In accordance with the preferred embodiment of the invention, the first transmit firing is used for initialization. For each receive channel in the receive beamformer, the receive signal derived from the first transmit firing of the packet will be subtracted from each receive signal derived from each subsequent transmit firing of the packet. The difference signals represent the wall-filtered, i.e., flow signals.

In the case of the first transmit firing of the packet, the resulting ultrasound echo signal detected by a particular transducer element is transduced into an RF receive signal and input to a pre-amplifier 42 of the corresponding receive channel connected to that transducer element. The output of pre-amplifier 42 is connected to a first input of a subtraction circuit 44. The second input of the subtraction circuit 44 is connected to a switch 56. For the first transmit firing, the switch 56 is open, i.e., is set to terminal "b", and no signal is provided to the second input of the subtraction circuit 44. Thus, the subtraction circuit 44 passes the pre-amplified receive signal derived from the first transmit firing substantially unaltered.

The pre-amplified receive signal for the first transmit firing is then input to a TGC amplifier 46. The TGC amplifier provides gain adjustment in the axial direction. The adjustment is made by increasing or decreasing gain as a function of depth. The gain provided by the TGC amplifier is controlled by the system operator via a lever on the operator interface. The output of the TGC amplifier is connected to the input of an analog-to-digital converter 48, which converts the amplified analog receive signal into digital samples. The digital samples output by the analog-to-digital converter 48 form a first receive vector (derived from the first transmit firing).

The first receive vector is used to initialize the wall-filtering circuit. This is accomplished by inputting the first receive vector to a digital gain adjustment circuit 50, which attenuates the first receive vector as a function of depth (range) to substantially remove the gain applied by the TGC amplifier 46. The gain-adjusted first receive vector is then stored in a random access memory (RAM) 52.

The transmitter then controls the transducer array to activate the second transmit firing. Again the resulting RF receive signal from the particular transducer element connected to the receive channel depicted in FIG. 4 is input to pre-amplifier 42. In synchronism with the start of the second receive signal, the switch 56 is closed, i.e., set to terminal "a", and the gain-adjusted first receive vector is read out of the RAM 52 and inputted to a digital-to-analog converter 54. The digital-to-analog converter 54 converts the first receive vector into a reconstructed analog receive signal substantially the same as the first receive signal. The reconstructed first receive signal is then passed through switch 56 and inputted to the second input of the subtraction circuit 44, which subtracts the reconstructed first receive signal from the second receive signal to form a first difference signal. The first difference signal is then amplified by the TGC amplifier 46 as a function of the depth of the transmit focal position for the first and second transmit firings; and converted into a flow vector by the analog-to-digital converter 48. The flow vector is then sent to the beamsummer to be added to the corresponding flow vectors from the other receive channels. It should be noted that in accordance with the preferred embodiment, the flow vector is not stored in RAM 52.

The procedure for processing the second receive signal can be repeated for additional subsequent receive signals derived from subsequent transmit firings in the packet. A new flow image can be formed for each subsequent transmit firing. Alternatively, every n-th transmit firing in a packet, where n>2, can be used for initialization, with the receive signal derived from the n-th firing being subtracted from the receive signals from the (n+1)-th to the (2n−1)-th firings to generate respective wall-filtered signals. In this case, (n−1) flow images are displayed for each packet of n transmit firings.

After wall filtering in the receive channels, the wall-filtered signals undergo analog-to-digital conversion to form respective flow vectors. The flow vectors are beamsummed and then processed in conventional fashion. In the case where wall filtering is incorporated in the receive channels of the beamformer 4, the wall filter 10 can be eliminated (see FIGS. 1 and 3).

The resulting flow image can be combined with a B-mode tissue image for concurrent display. For example, for each receive channel the receive vector derived from the initializing transmit firing can be processed in conventional fashion to form a grayscale tissue image. Subsequently, the flow vectors are used to create a flow image which is superimposed on the tissue image. The flow image can be either a color image or a grayscale image.

The receive channel in accordance with the preferred embodiments of the invention operates under the control of the host computer 20 (see FIG. 4) or a dedicated processor. In particular, the host computer 20 sets the attenuation level in the gain adjustment circuit 50 in dependence on the TGC amplifier gain setting, controls the writing into and reading out of the RAM 52, and controls the switching of switch 56 in synchronism with the host computer's control of the transmitter so that the reconstructed receive signal from the previous transmit firing is input to the subtraction circuit 44 concurrently with the input of the receive signal derived from the current transmit firing.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. For example, numerous different hardware configurations can be used to implement wall filtering in the receive channels. For example, instead of using a subtraction circuit, it is possible to flip the sign bit of (i.e., invert) the receive vector stored in the RAM 52 and then add the inverted analog signal to the current RF receive signal. Also, the switch 56 can be eliminated if the RAM 52 can be set to output a signal level equivalent to 0 V. Therefore, it is intended that the invention not be limited to the particular embodiment disclosed as the best mode contemplated for carrying out this invention, but that the invention will include all embodiments falling within the scope of the appended claims.

What is claimed is:

1. A system for imaging flowing matter, comprising:
an array of transducer elements;
a receiver comprising a multiplicity of receive channels, each receive channel being coupled to a respective transducer element during first and second receive cycles for receiving first and second analog signals representing ultrasound echoes detected by said respective transducer element, and outputting a digital signal representing a difference between said first and second analog signals, and a beamsummer for beamsumming said digital signals output by said receive channels to form a flow vector which is a function of the velocity of flowing matter along a receive line;
a processor for deriving a flow image vector from said flow vector; and
a display subsystem for displaying a flow image having an image portion which is a function of said flow image vector.

2. The system as recited in claim 1, wherein said processor comprises an envelope detector.

3. The system as recited in claim 1, wherein said processor comprises a parameter estimator.

4. The system as recited in claim 1, wherein said transducer elements are piezoelectric transducer elements.

5. The system as recited in claim 1, wherein each receive channel comprises a pre-amplifier, a subtraction circuit, a time-gain control amplifier and an analog-to-digital converter arranged in series, and a receive signal reconstructing circuit arranged to receive an output from said analog-to-digital converter during said first receive cycle and to supply a reconstructed first analog signal to a first input of said subtraction circuit during said second receive cycle, said subtraction circuit having a second input coupled to an output of said pre-amplifier and having an output coupled to an input of said time-gain control amplifier.

6. The system as recited in claim 5, wherein said receive signal reconstructing circuit comprises memory for storing a receive vector derived from a signal output by said analog-to-digital converter during said first receive cycle and a digital-to-analog converter having an input coupled to said memory and having an output coupled to said first input of said subtraction circuit.

7. The system as recited in claim 6, wherein said receive signal reconstructing circuit further comprises a gain adjustment circuit arranged between said memory and the output of said analog-to-digital converter.

8. The system as recited in claim 6, wherein said receive signal reconstructing circuit further comprises a switch arranged between an output of said digital-to-analog converter and said first input of said subtraction circuit.

9. The system as recited in claim 1, wherein said receive channel circuitry comprises a pre-amplifier, a summation circuit, a time-gain control amplifier and an analog-to-digital converter arranged in series, and a receive signal reconstructing circuit arranged to receive an output from said analog-to-digital converter during said first receive cycle and to supply an inverted reconstructed first analog signal to a first input of said summation circuit during said second receive cycle, said summation circuit having a second input coupled to an output of said pre-amplifier and having an output coupled to an input of said time-gain control amplifier.

10. A receive channel in an ultrasound imaging system, comprising a pre-amplifier, a subtraction circuit, a time-gain control amplifier and an analog-to-digital converter arranged in series, and a receive signal reconstructing circuit arranged to receive an output from said analog-to-digital converter and to supply a reconstructed analog signal to a first input of said subtraction circuit, said subtraction circuit having a second input coupled to an output of said pre-amplifier and having an output coupled to an input of said time-gain control amplifier.

11. The receive channel as recited in claim 10, wherein said receive signal reconstructing circuit comprises memory for storing a digital signal derived from the output of said analog-to-digital converter and a digital-to-analog converter having an input coupled to said memory and having an output coupled to said first input of said subtraction circuit.

12. The receive channel as recited in claim 11, wherein said receive signal reconstructing circuit further comprises a gain adjustment circuit arranged between said memory and the output of said analog-to-digital converter.

13. The receive channel as recited in claim 12, wherein said receive signal reconstructing circuit further comprises a switch arranged between an output of said digital-to-analog converter and said first input of said subtraction circuit.

14. A receive channel in an ultrasound imaging system, comprising a pre-amplifier, a summation circuit, a time-gain control amplifier and an analog-to-digital converter arranged in series, and a receive signal reconstructing circuit arranged to receive an output from said analog-to-digital converter and to supply an inverted reconstructed analog signal to a first input of said summation circuit, said summation circuit having a second input coupled to an output of said pre-amplifier and having an output coupled to an input of said time-gain control amplifier.

15. A system for imaging flowing matter, comprising:
a transducer array comprising a multiplicity of transducer elements;
a transmitter coupled to said transducer array for pulsing selected transducer elements during first and second transmit firings to produce first and second transmit beams of wave energy focused at a transmit focal position;
a receiver comprising a multiplicity of receive channels respectively coupled to selected transducer elements of said transducer array for receiving a respective set of electrical receive signals transduced subsequent to each transmit firing, and a beamsummer for beamsumming receive vectors output by said receive channels, each receive channel comprising means for forming a flow vector which is a function of a difference between first and second receive signals acquired following said first and second transmit firings respectively, and said beamsummer forming a beamsummed flow vector from said flow vectors;
a processor for deriving a flow image vector from said beamsummed flow vector; and
a display subsystem for displaying a flow image having an image portion which is a function of said flow image vector.

16. A method for wall filtering receive signals in a receive channel of an imaging system, comprising the steps of:
(a) subjecting a first receive signal input to said receive channel to analog-to-digital conversion to form a receive vector;
(b) storing said receive vector;
(c) subjecting said receive vector to digital-to-analog conversion to form a reconstructed first receive signal;
(d) subtracting said reconstructed first receive signal from a second receive signal input to said receive channel to form a flow signal; and
(e) subjecting said flow signal to analog-to-digital conversion to form a flow vector.

17. The method as recited in claim 16, further comprising the steps of:
amplifying said first receive signal before analog-to-digital conversion;
attenuating said first receive vector before storing; and
amplifying said flow signal before analog-to digital conversion.

18. A method for wall filtering receive signals in a receive channel of an imaging system, comprising the steps of:
(a) subjecting a first receive signal input to said receive channel to analog-to-digital conversion to form a receive vector;
(b) inverting said receive vector;
(c) subjecting said inverted receive vector to digital-to-analog conversion to form a reconstructed inverted first receive signal;
(d) summing said reconstructed inverted first receive signal and a second receive signal input to said receive channel to form a flow signal; and
(e) subjecting said flow signal to analog-to-digital conversion to form a flow vector.

19. An imaging system comprising:
a transducer array comprising a multiplicity of transducer elements for transmitting wave energy in response to electrical activation and transducing returned wave energy into electrical signals;
a display monitor for displaying a flow image having an image portion which is a function of a flow image vector; and
a computer programmed to perform the following steps:
(a) activating transducer elements of said array to transmit focused wave energy during first and second transmit firings;
(b) forming first and second sets of receive signals from electrical signals output from said transducer elements subsequent to said first and second transmit firings respectively;
(c) for each pair of receive signals from said first and second sets corresponding to a respective transducer element, forming a respective flow vector which is a function of a difference between said pair of receive signals, said respective flow vectors forming a set;
(d) beamsumming said set of flow vectors to form a beamsummed flow vector;
(e) forming a flow image signal derived at least in part from said beamsummed flow vector; and
(f) sending said flow image signal to said display monitor.

20. An imaging system comprising:
a transducer array comprising a multiplicity of transducer elements for transmitting wave energy in response to electrical activation and transducing returned wave energy into electrical signals;
a transmitter coupled to said transducer array for pulsing selected transducer elements during first and second transmit firings to produce first and second transmit beams of wave energy focused at a transmit focal position;
a receiver comprising a multiplicity of receive channels respectively coupled to selected transducer elements of said transducer array for receiving first and second sets of electrical receive signals transduced subsequent to said first and second transmit firings respectively, each receive channel comprising means for forming a respective flow vector which is a function of a difference between a respective pair of receive signals from said first and second sets corresponding to a respective transducer element, said respective flow vectors from all receive channels forming a set, and said receiver further comprising a beamsummer for beamsumming said set of flow vectors to form a beamsummed flow vector;

a processor for deriving an image vector from said beamsummed flow vector; and a display subsystem for displaying an image having an image portion which is a function of said image vector.

21. A method of flow imaging, comprising the steps of:

transmitting first and second beams of wave energy from transducer elements of an array forming a transmit aperture during first and second transmit firings respectively, said first and second beams being focused at a transmit focal position;

receiving first and second sets of receive signals subsequent to said first and second transmit firings respectively, each set comprising one receive signal for each transducer element in a receive aperture;

for each transducer element in said receive aperture, forming a respective flow vector which is a function of a difference between a respective pair of receive signals from said first and second sets corresponding to said respective transducer element, said respective flow vectors forming a set;

beamsumming said set of flow vectors to form a beamsummed flow vector;

deriving an image vector from said beamsummed flow vector; and displaying an image having an image portion which is a function of said image vector.

22. The method as recited in claim 21, wherein said step of forming a respective flow vector comprises the steps of:

(a) subjecting a receive signal of said first set to analog-to-digital conversion to form a receive vector;

(b) storing said receive vector;

(c) subjecting said receive vector to digital-to-analog conversion to form a reconstructed receive signal of said first set;

(d) subtracting said reconstructed receive signal of said first set from a receive signal of said second set to form a flow signal; and (e) subjecting said flow signal to analog-to-digital conversion to form said respective flow vector.

23. The method as recited in claim 21, wherein said step of forming a respective flow vector comprises the steps of:

(a) subjecting a receive signal of said first set to analog-to-digital conversion to form a receive vector;

(b) inverting said receive vector;

(c) subjecting said inverted receive vector to digital-to-analog conversion to form a reconstructed inverted receive signal of said first set;

(d) summing said reconstructed inverted receive signal of said first set from a receive signal of said second set to form a flow signal; and (e) subjecting said flow signal to analog-to-digital conversion to form said respective flow vector.

* * * * *